US012205694B2

(12) United States Patent
Kapaldo

(10) Patent No.: US 12,205,694 B2
(45) Date of Patent: Jan. 21, 2025

(54) ARTIFICIAL INTELLIGENCE BASED SYSTEMS AND METHODS CONFIGURED TO IMPLEMENT PATIENT-SPECIFIC MEDICAL ADHERENCE INTERVENTION

(71) Applicant: WALGREEN CO., Deerfield, IL (US)

(72) Inventor: James Even Kapaldo, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 243 days.

(21) Appl. No.: 16/792,750

(22) Filed: Feb. 17, 2020

(65) Prior Publication Data

US 2021/0241873 A1  Aug. 5, 2021

Related U.S. Application Data

(60) Provisional application No. 62/969,464, filed on Feb. 3, 2020.

(51) Int. Cl.
*G16H 20/10* (2018.01)
*G06N 5/04* (2023.01)
(Continued)

(52) U.S. Cl.
CPC .............. *G16H 20/10* (2018.01); *G06N 5/04* (2013.01); *G06N 20/00* (2019.01); *G06Q 10/107* (2013.01);
(Continued)

(58) Field of Classification Search
CPC ........ G16H 20/10; G16H 40/67; G16H 50/30; G16H 50/70; G06N 20/00; G06N 5/04; G06Q 10/107
See application file for complete search history.

(56) References Cited

U.S. PATENT DOCUMENTS 11,222,094 B1 *  1/2022  Walton ................. G16H 20/10
11,631,484 B1 *  4/2023  Hanina ................. G16H 80/00
                                                              706/11
(Continued)

FOREIGN PATENT DOCUMENTS

WO  WO-2020002284 A1 *  1/2020  ............... G06N 5/02
WO  WO-2020068727 A1 *  4/2020  ............. G06F 15/18

OTHER PUBLICATIONS

Helios Solutions—How AI Powered Medicationreminder App Can Boost Adherence?—https://www.heliossolutions.co/blog/ai-powered-medication-reminder-app-can-boost-adherence/—2017 (Year: 2017).*
(Continued)

*Primary Examiner* — Jonathon A. Szumny
(74) *Attorney, Agent, or Firm* — MARSHALL, GERSTEIN & BORUN LLP; Randall G. Rueth

(57) ABSTRACT

Artificial Intelligence (AI) based systems and methods are disclosed for implementing patient-specific medical adherence intervention. An AI model is trained on a first set of data comprising (1) patient data defining a plurality of medical patients having respective prescribed medications and (2) intervention communication data. During a first iteration of a medication adherence session, a second set of data comprising patient data of a new or existing medical patient is received and input by the AI model to generate a medical adherence intervention prediction defining at least a preferred intervention channel specific to the new or existing medical patient. An electronic medical adherence intervention communication, is generated, and related correspondence is sent, to the new or existing medical patient based on (1) the medical adherence intervention prediction and (2) an intervention template corresponding to the preferred intervention channel.

42 Claims, 5 Drawing Sheets

(51) Int. Cl.
*G06N 20/00* (2019.01)
*G06Q 10/107* (2023.01)
*G16H 40/67* (2018.01)
*G16H 50/30* (2018.01)
*G16H 50/70* (2018.01)

(52) U.S. Cl.
CPC ............ *G16H 40/67* (2018.01); *G16H 50/30* (2018.01); *G16H 50/70* (2018.01)

(56) References Cited

U.S. PATENT DOCUMENTS

| | | | |
|---|---|---|---|
| 2012/0095798 A1* | 4/2012 | Mabari | G06Q 10/0637 705/7.17 |
| 2013/0222135 A1* | 8/2013 | Stein | A61J 7/0436 222/23 |
| 2015/0061832 A1* | 3/2015 | Pavlovic | G06V 20/66 340/5.83 |
| 2015/0100335 A1* | 4/2015 | Englehard | G16H 40/67 705/2 |
| 2015/0100343 A1* | 4/2015 | Siedlecki | G16H 20/10 705/2 |
| 2015/0193594 A1 | 7/2015 | Lara et al. | |
| 2015/0248540 A1* | 9/2015 | Lovejoy | G16H 40/67 706/47 |
| 2016/0015602 A1* | 1/2016 | Panzini | A61J 7/0481 206/534 |
| 2016/0203290 A1* | 7/2016 | An | G16H 40/67 705/2 |
| 2017/0228520 A1 | 8/2017 | Kidd et al. | |
| 2017/0283873 A1* | 10/2017 | Rico | C12Q 1/6886 |
| 2019/0341130 A1 | 11/2019 | Kaukab et al. | |
| 2020/0004583 A1 | 1/2020 | Kelly et al. | |
| 2020/0085312 A1* | 3/2020 | Tzvieli | A61B 5/02055 |
| 2020/0097651 A1* | 3/2020 | Mestha | G06F 21/554 |
| 2020/0098456 A1* | 3/2020 | Loscutoff | G06F 9/542 |
| 2020/0111044 A1* | 4/2020 | New, Jr. | G06Q 10/063112 |
| 2020/0126650 A1* | 4/2020 | Loscutoff | G16H 10/60 |
| 2020/0185104 A1* | 6/2020 | Zhu | G06Q 20/405 |
| 2020/0327962 A1* | 10/2020 | Chittenden | G16B 20/00 |
| 2021/0350910 A1* | 11/2021 | Dastmalchi | G06Q 10/067 |

OTHER PUBLICATIONS

Labovitz et al., "Using Artificial Intelligence to Reduce the Risk of Nonadherence in Patients on Anticoagulation Therapy," Stroke. May 2017; 48(5): 1416-1419. (Year: 2017).*

European Patent Application No. 21154540.5, Extended European Search Report, dated Jul. 14, 2021.

European Patent Application No. 21154540.5, Communication Pursuant to Article 93(3) EPC, dated Apr. 23, 2024.

* cited by examiner

| PATIENT 302 | CONDITION 304 | COVERAGE 306 | PATIENT BEHAVIOR 308 | TIME/GEO 310 | MEDICATION 312 |
|---|---|---|---|---|---|
| ETHNICITY | SEVERITY | MEDICATION COST | PURCHASE HISTORY | TIME OF YEAR | SIZE OF TABLET |
| AGE | REQUIRED MEDICATION | INSURANCE COMPANY | VISIT FREQUENCY | HOLIDAY | LIQUID/TABLET/ INJECTION |
| GENDER | NUMBER OF REQUIRED MEDICATIONS | CHANGE IN INSURANCE PLAN | VISIT CONSISTENCY | VACATION SEASON | TASTE OF MEDICATION IF ORAL |
| INCOME | MEDICATION FREQUENCY | TOTAL OUT OF POCKET FOR ALL MEDICATIONS (INDIVIDUAL & FAMILY) | | WEATHER | SEVERITY OF SIDE EFFECTS |
| KNOWLEDGE OF ILLNESS/ TREATMENT | SYMPTOMS | | | VERY COLD/HOT | EASE OF ADMINISTRATION |
| LOCATION | ELAPSED TIME IN CONDITION | | | RAIN/SNOW SEASON | |

FIG. 3

ARTIFICIAL INTELLIGENCE BASED SYSTEMS AND METHODS CONFIGURED TO IMPLEMENT PATIENT-SPECIFIC MEDICAL ADHERENCE INTERVENTION

CROSS REFERENCE TO RELATED APPLICATIONS

This application claims the benefit of U.S. Provisional Application No. 62/969,464 (filed on Feb. 3, 2020). The entirety of the foregoing provisional application is incorporated by reference herein.

FIELD OF THE DISCLOSURE

The present disclosure generally relates to systems and methods for implementing digital solutions regarding patient medical adherence intervention, and, more particularly, to artificial intelligence (AI) based systems and methods for implementing patient-specific medical adherence intervention.

BACKGROUND

Medical adherence may generally be defined as the degree to which a medical patient's behavior corresponds with agreed recommendations from a health care provider. Generally, medical adherence regards a patient's compliance in taking, filling, or administering a medicine, pharmaceutical product, prescription, or other medical treatment. More specifically, medical adherence can be a measure between 0 and 1 (0% to 100%); 0 meaning that the patient did not fill any prescription, and 1 meaning the patient took their medication as prescribed during his or her treatment period. An accepted and standard approximate measurement of medical adherence (or "adherence") is the "proportion of days covered" (PDC), which computes the fraction of days a patient is covered (has effective medication) to treat a condition. Some conditions can be treated equally effectively by more than one medication, e.g., if the patient has any one of a given set of medications on a given day, then the patient is considered covered (i.e., medically adherent) on that day. Other conditions, however, may require multiple medications to be taken concurrently; for example, if a condition requires three different medications, and a patient only has two of them on a given day, then the patient is not considered covered (i.e., not medically adherent) on the particular day.

A problem arises with respect to patients who do not take their prescriptions as prescribed (i.e., patients who are non-adherent). Such patients may become at risk for costly and/or serious issues, including incurring additional or progressive medical conditions and/or requiring additional medication or treatment(s) to treat such additional or progressive medical conditions. Because of this, insurance companies typically offer incentives to pharmacies, or other such medical providers, for each patient who is adherent. For example, such incentives may be provided at the end of a calendar year or otherwise.

However, it is generally difficult to determine which, if any, medical adherence program will be successful with any given patient. Medical patients may respond to medical adherence programs in different ways (or, in some cases, not at all). For example, a first medical adherence program that may increase medical adherence for one patient may have no effect on another, different patient. No current system exists that efficiently and effectively provides medical adherence intervention or compliance on a patient-specific basis.

For the foregoing reasons, there is a need for AI based systems and methods for implementing patient-specific medical adherence intervention.

BRIEF SUMMARY

The AI based systems and methods described herein are configured to provide patient-specific medical adherence intervention through a highly scalable AI based (e.g., machine learning based) framework for continuously identifying patients who are likely to be non-adherent. In addition, the AI based systems and methods provide techniques to automatically determine effective methods for intervening with non-adherent patients in such a way that they become adherent. In various embodiments, the AI based systems and methods use advanced AI methodologies to determine when and how to intervene by, e.g., automatically and continually creating and testing, through the execution of a ensemble based AI framework, new procedures of intervening, and for specific patients. The AI based systems and methods may input patient-specific data, medication related data, and other data to determine adherence metrics such as when, how, how many times, and in what combinations of interaction modes, channels, and/or intervals to intervene with specific patients.

In addition, the AI based systems and methods may be implemented to analyze new emerging intervention correspondence or procedures. For example, the AI based systems and methods may be implemented to discover new intervention strategies, while at the same time maintaining a required threshold successful intervention rate. The AI based systems and methods measure successful intervention rate through a variety of metrics, where, adherence predicted (e.g., as a dependent variable) for specific patients based on specific feature data (e.g., independent feature data), e.g., including specific patient data or data that is related, or assumed to be related, to the specific patient.

Accordingly, in various embodiment disclosed herein, the present disclosure describes an AI based system configured to implement patient-specific medical adherence intervention. The AI based system comprises a computer memory configured to store one or more intervention templates. Each of the one or more intervention templates may correspond to an intervention channel. The AI based system may further comprise an intervention server that includes one or more processors that communicatively coupled to the computer memory. The intervention server is configured to access the one or more intervention templates. The AI based system may further comprise a medical adherence AI model trained on a first set of data comprising (1) patient data defining a plurality of medical patients having respective prescribed medications and (2) intervention communication data. Each medical patient as identified within the patient data may be assigned at least one intervention channel as identified within the intervention communication data. The AI based system may further comprise electronic instructions stored on the computer memory that when executed by the one or more processors cause the one or more processors, during a first iteration of a medication adherence session, to: receive a second set of data comprising a second set of patient data, the second set of patient data comprising patient data of a new or existing medical patient; generate, by the medical adherence AI model inputting the second set of patient data, a medical adherence intervention prediction defining at least a preferred intervention channel specific to the new or existing medical patient; generate an electronic medical adherence intervention communication specific to the new or existing medical patient, the electronic medical adherence intervention communication based on (1) the medical adherence intervention prediction and (2) an intervention template of the one or more intervention templates corresponding to the preferred intervention channel; and, initiate a correspondence of the electronic medical adherence intervention communication, the correspondence comprising information regarding administration of a medication for treatment of a medical condition specific to the new or existing medical patient.

In additional embodiments, an AI based method is disclosed for implementing patient-specific medical adherence intervention. The AI based method may include storing, in a computer memory, one or more intervention templates. Each of the one or more intervention templates may correspond to an intervention channel. The AI based method may further include training, by one or more processors, a medical adherence AI model on a first set of data. The first set of data may comprise (1) patient data defining a plurality of medical patients having respective prescribed medications and (2) intervention communication data. Each medical patient, as identified within the patient data, may be assigned to at least one intervention channel, as identified within the intervention communication data. The AI based method may further include receiving, at the one or more processors during a first iteration of a medication adherence session, a second set of data comprising a second set of patient data. The second set of patient data may comprise patient data of a new or existing medical patient. The AI based method may further include generating, by the medical adherence AI model inputting the second set of patient data during the first iteration, a medical adherence intervention prediction defining at least a preferred intervention channel specific to the new or existing medical patient. The AI based method may further include generating, by the one or more processors during the first iteration, an electronic medical adherence intervention communication specific to the new or existing medical patient, the electronic medical adherence intervention communication based on (1) the medical adherence intervention prediction and (2) an intervention template of the one or more intervention templates corresponding to the preferred intervention channel. The AI based method may further include initiating, by the one or more processors during the first iteration, a correspondence of the electronic medical adherence intervention communication. The correspondence may comprise information regarding administration of a medication for treatment of a medical condition specific to the new or existing medical patient.

In a still further embodiments, a tangible, non-transitory computer-readable medium stores instructions for implementing patient-specific medical adherence intervention, that when executed by one or more processors cause the one or more processors to store, in a computer memory, one or more intervention templates. Each of the one or more intervention templates may correspond to an intervention channel. The instructions, when executed by the one or more processors, further cause the one or more processors to train a medical adherence AI model on a first set of data, the first set of data comprising (1) patient data defining a plurality of medical patients having respective prescribed medications and (2) intervention communication data. Each medical patient, as identified within the patient data, is assigned at least one intervention channel as identified within the intervention communication data. The instructions, when executed by the one or more processors, further cause the one or more processors to receive, at the one or more processors during a first iteration of a medication adherence session, a second set of data comprising a second set of patient data. The second set of patient data may comprise patient data of a new or existing medical patient. The instructions, when executed by the one or more processors, further cause the one or more processors to generate, by the medical adherence AI model inputting the second set of patient data during the first iteration, a medical adherence intervention prediction defining at least a preferred intervention channel specific to the new or existing medical patient. The instructions, when executed by the one or more processors, further cause the one or more processors to generate, by the one or more processors during the first iteration, an electronic medical adherence intervention communication specific to the new or existing medical patient, the electronic medical adherence intervention communication based on (1) the medical adherence intervention prediction and (2) an intervention template of the one or more intervention templates corresponding to the preferred intervention channel. The instructions, when executed by the one or more processors, further cause the one or more processors to initiate, by the one or more processors during the first iteration, a correspondence of the electronic medical adherence intervention communication. The electronic correspondence comprises information regarding administration of a medication for treatment of a medical condition specific to the new or existing medical patient.

In accordance with the above, and with the disclosure herein, the present disclosure includes improvements in computer functionality or in improvements to other technologies at least because the claims recite that, e.g., a medical adherence AI model that improves the predictive capabilities of a given computer or other technologies. That is, the present disclosure describes improvements in the functioning of the computer itself or "any other technology or technical field" because the medical adherence AI model is able to more accurately predict patient-specific medical adherence interventions, including customized, electronic medical adherence intervention communications specific to new or existing medical patients regarding administration of medication for treatment of medical conditions specific to those respective patients. This improves over the prior art at least because the underlying computer, system, or "any other technology or technical field" is able to operate with fewer processor and/or memory resources, e.g., as each electronic medical adherence intervention communication is customized for specific users. Thus, the underlying systems are not required to track, process, and store data for all patients over a multitude of medical adherence technical interventions and related communications, many of which would likely be ineffective, and, thus, a waste to the computational and storage resources of the underlying system.

In addition, the present disclosure implements an AI model architecture that improves over conventional AI models that rely on a single aggregation or transformation/compression method with a single model. Such conventional AI models can be extremely difficult to effectively train across various data samples (e.g. patient/medication combinations as described herein). In contrast, the AI model architecture described herein improves over the conventional AI models, executing on the underlying system, by implementing an ensemble based framework that comprises a unique and efficient process involving data aggregation, data transformation/compression, an ensemble of different models, and then model result unification to combine the large number of resulting predictions into a single predicted output. This enhanced AI model architecture improves an underlying computing system by implementing and creating an overall model that has the ability to accurately predict and generalize new data for the majority (if not all) data samples. This not only improves the accuracy of the underlying computer system, but also reduces the memory and/or processing of the system, over time, as the AI model architecture is able to more quickly, and efficiently, determine an accurate predictive model compared with conventional single model architectures.

In addition, the present disclosure includes specific features other than what is well-understood, routine, conventional activity in the field, or adding unconventional steps that confine the claim to a particular useful application, e.g., implementing AI based patient-specific medical adherence intervention as described herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIG. 3 illustrates a diagram including example feature data that may be used to train a medical adherence artificial intelligence model, in accordance with various embodiments disclosed herein.

The Figures depict preferred embodiments for purposes of illustration only. Alternative embodiments of the systems and methods illustrated herein may be employed without departing from the principles of the invention described herein.

DETAILED DESCRIPTION

Figure 1:
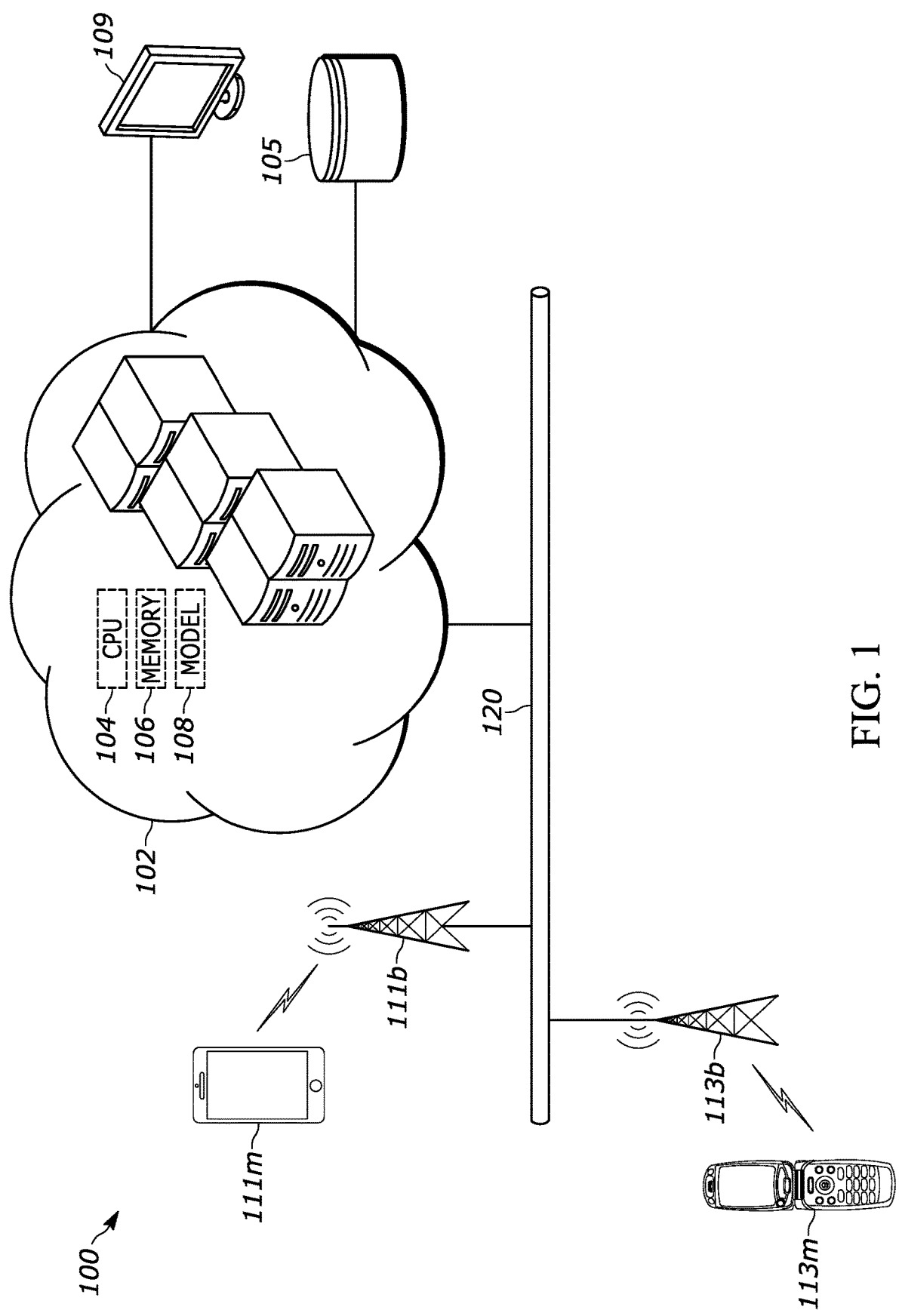
FIG. 1 illustrates an artificial intelligence (AI) based platform configured to implement patient-specific medical adherence intervention in accordance with various embodiments disclosed herein.

FIG. 1 illustrates an artificial intelligence (AI) based platform 100 configured to implement patient-specific medical adherence intervention in accordance with various embodiments disclosed herein. In the example embodiment of FIG. 1, AI based platform 100 includes server(s) 102, which may be referred to herein as "intervention server(s)," and which may comprise one or more computer servers. In various embodiments, server(s) 102 comprise multiple servers, which may comprise multiple, redundant, or replicated servers as part of a server farm. In still further embodiments, server(s) 102 are implemented as cloud-based servers. For example, server(s) 102 may be a cloud-based platform such as MICROSOFT AZURE, AMAZON AWS, or the like.

Server(s) 102 may include one or more processor(s) 104 as well as one or more computer memories 106. The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories 106 may store an operating system (OS) (e.g., Microsoft Windows, Linux, Unix, etc.) capable of facilitating the functionalities, apps, methods, or other software as discussed herein. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, the machine learning component and/or the provisioning application, where each are configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 105 (e.g., a relational database, such as Oracle, DB2, MySQL, or a NoSQL based database, such as MongoDB). The data stored in the memories 106 and/or the database 105 may include all or part of any of the data or information described herein, including, for example, the one or more search requests, the one or more transaction details, and the profile information of the user.

The server(s) 102 may further include a communication component configured to communicate (e.g., send and receive) data via one or more external/network port(s) to one or more networks or local terminals, such as computer network 120 and/or terminal 109 (for rendering or visualizing) as described herein. In some embodiments, server(s) 102 may include a client-server platform technology such as ASP.NET, Java J2EE, Ruby on Rails, Node.js, a web service or online API, responsive for receiving and responding to electronic requests. The server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120.

Server(s) 102 may further include or implement an operator interface configured to present information to an administrator or operator and/or receive inputs from the administrator or operator. As shown in FIG. 1, an operator interface may provide a display screen (e.g., via terminal 109). Server(s) 102 may also provide I/O components (e.g., ports, capacitive or resistive touch sensitive input panels, keys, buttons, lights, LEDs), which may be directly accessible via or attached to server(s) 102 or may be indirectly accessible via or attached to terminal 109. According to some embodiments, an administrator or operator may access the server(s) 102 via terminal 109 to review information, make changes, input training data, and/or perform other functions.

As described above herein, in some embodiments, server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, or application, (e.g., the medical adherence application (app)) in accordance with some embodiments may include a computer usable storage medium, or tangible, non-transitory computer-readable medium (e.g., standard random access memory (RAM), an optical disc, a universal serial bus (USB) drive, or the like) having computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, Actionscript, Javascript, HTML, CSS, XML, etc.).

In the example embodiment of FIG. 1, intervention server(s) 102 are communicatively connected, via computer network 120 and base stations 111b and 113b to respective mobile devices 111m and 113m. Computer network 120 may comprise a packet based network operable to transmit computer data packets among the various devices and servers described herein. For example, computer network 120 may consist of any one or more of Ethernet based network, a private network, a local area network (LAN), and/or a wide area network (WAN), such as the Internet. In addition, in some embodiments, computer network 120 may comprise cellular or mobile networks to facilitate data packet traffic (e.g., mobile device movement data) to and from base stations 111b and/or 113b. Base stations 111b and 113b may comprise cellular towers or access points implementing any one or more cellular or mobile device standards, including, for example, any of GSM, UMTS, CDMA, NMT, LTE, 5G NR, or the like.

As shown in FIG. 1, intervention server(s) 102 and/or their respective memorie(s) 106 are configured to store one or more intervention templates. In various embodiments, an intervention server is configured to access, e.g., via processor 104, the one or more intervention templates in memory 106. In various embodiments, an intervention template comprises an electronic template that may include characters, text, images, graphics, videos, or other such media that may be used for the generation of electronic medical adherence intervention communication(s) as described herein. For example, in various embodiments, a template may be merged or combined with patient data of a medical patient for the generation, creation, or otherwise implementation of patient-specific medical adherence intervention. A template may include placeholders or data fields that digitally accept new data, such as patient data or medical data in order to customize a communication or correspondence to a specific patient or patient group.

In various embodiments, each of the one or more intervention templates generally correspond to an intervention channel, which can be a type of communication or a physical or logical channel for transmitting or invoking a correspondence to a medical patient. An intervention channel, for example, comprises any of, e.g., a telephone communication, a text message, an in-app communication, or an email, which may be transmitted or otherwise established, e.g., via computer network 120 from server(s) 102. Although, it is to be appreciated that such channels may utilize other infrastructure for communication, such as standard telephone communications, cellular communication, U.S. postal mail, or the like.

In various embodiments, a medical adherence artificial intelligence model 108 is trained on a first set of data. The first set of data may include patient data defining one or more medical patients. Each of the medical patients may have respective prescribed medications, such as pharmaceutical products to treat a diagnosed medical condition, ailment, or other medical event. The first set of data may also include intervention communication data. The first set of data may comprise feature training data, which may include compressed and/or transformed data, for training medical adherence artificial intelligence model 108. Other data or datasets are described herein, for example, for FIG. 3. Training medical adherence artificial intelligence model 108 may include inputting a dataset (e.g., first set of data) into an AI training algorithm or platform, such as TENSORFLOW or PYTORCH.

In various embodiments, medical adherence artificial intelligence model 108 is trained using a supervised or unsupervised machine learning program or algorithm. The machine learning program or algorithm may employ a neural network, which may be a convolutional neural network, a deep learning neural network, or a combined learning module or program that learns in two or more features or feature datasets in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. Machine learning may involve identifying and recognizing patterns in existing data (such as datasets described herein, including patient data, intervention communication data, or other data, e.g., data as illustrated for FIG. 3 herein) in order to facilitate making predictions for subsequent data (e.g., to predict PDC or to generate, by the medical adherence AI model inputting a second set of patient data, a medical adherence intervention prediction defining at least a preferred intervention channel specific to the new and/or existing medical patient).

Machine learning model(s), such as medical adherence artificial intelligence model 108, may be created and trained based upon example (e.g., "training data,") inputs or data (which may be termed "features" and "labels"), as described herein, in order to make valid and reliable predictions for new inputs, such as testing level or production level data or inputs. For example, FIG. 3 illustrates a diagram including example feature data that may be used to train medical adherence artificial intelligence model 108. For example, as shown for FIG. 3, feature data may include anything of relevance, particularly features concerning the patient (302), medical condition (304), insurance coverage (306), patient behaviors (308), time/geo based features (310), and/or medication features (312). Several examples of such feature data are illustrated for FIG. 3.

In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

In some embodiments, each medical patient as identified within a set of patient data (e.g., a first set of data) may be assigned at least one intervention channel as identified within the intervention communication data. For example, a first patient may be assigned to a text based intervention channel where the first patient has provided approval to receive correspondence or communication via text message/ short message service (SMS) communication. As a further example, a second patient may be assigned both a text based intervention channel and a telephone based intervention channel where the second patient has provided approval to receive correspondence or communication via each of text message/SMS and telephone communications.

Such communications can be transmitted to a device of a medical patient. For example, with respect to FIG. 1, mobile devices 111*m* and 113*m* represent example devices of respective medical patients. Medical patients may receive correspondence of electronic medical adherence intervention communications (e.g., corresponding to intervention methods/types as described herein) via mobile devices 111*m* and 113*m* as received from base stations 111*b* and 113*b*, respectively, over computer network 120. In some embodiments, the electronic medical adherence intervention communications may be received by a mobile device (e.g., mobile device 111*m*) on a native application installed on the mobile device, such as a native SMS application implemented for Apple iOS or Google Android. Additionally, or alternatively, the electronic medical adherence intervention communications may be received by a medical adherence application (app) implemented on a device (e.g., mobile device 111*m*) of a medical patient. For example, a processor of a mobile device (e.g., mobile device 111*m*) may install and/or execute a medical adherence app on the mobile device. A medical adherence app may be implemented or programmed in SWIFT, Objective-C, Java, or other similar mobile app programming languages and may be designed to execute on a mobile operating systems, such as Apple iOS or Google Android. The medical adherence app may include a notification area (e.g., window) and/or an audible or a visual interface to interact, communicate, or otherwise provide information to a medical patient regarding administration of a medication for treatment of a medical condition as described herein. In additional embodiment, the medical adherence app may provide tracking data to track a patient's adherence or degree thereof. Such tracking data may be transmitted from a mobile device (e.g., mobile device 111*m*) to server(s) 102 for storage in database 105 and/or memorie(s) 106.

As described in various embodiments herein, correspondence of the electronic medical adherence intervention communication(s) may be executed or implemented (e.g., via processor 104 of intervention server(s) 102) during one or more iterations of an adherence session. An adherence session typically includes a time period over which a particular medication has been prescribed. For example, a patient may have been prescribed a medication that, when administered as expected, lasts approximately one month's time. The adherence session may last for approximately the same time, although different times or time periods (e.g., days, weeks, months, years, etc.) are contemplated herein, e.g., where an adherence session may be adjusted (e.g., extended or shortened) based on a patient's behavior or lack thereof (e.g., failing to take the medication during or over the prescribed time(s)).

Figure 2:
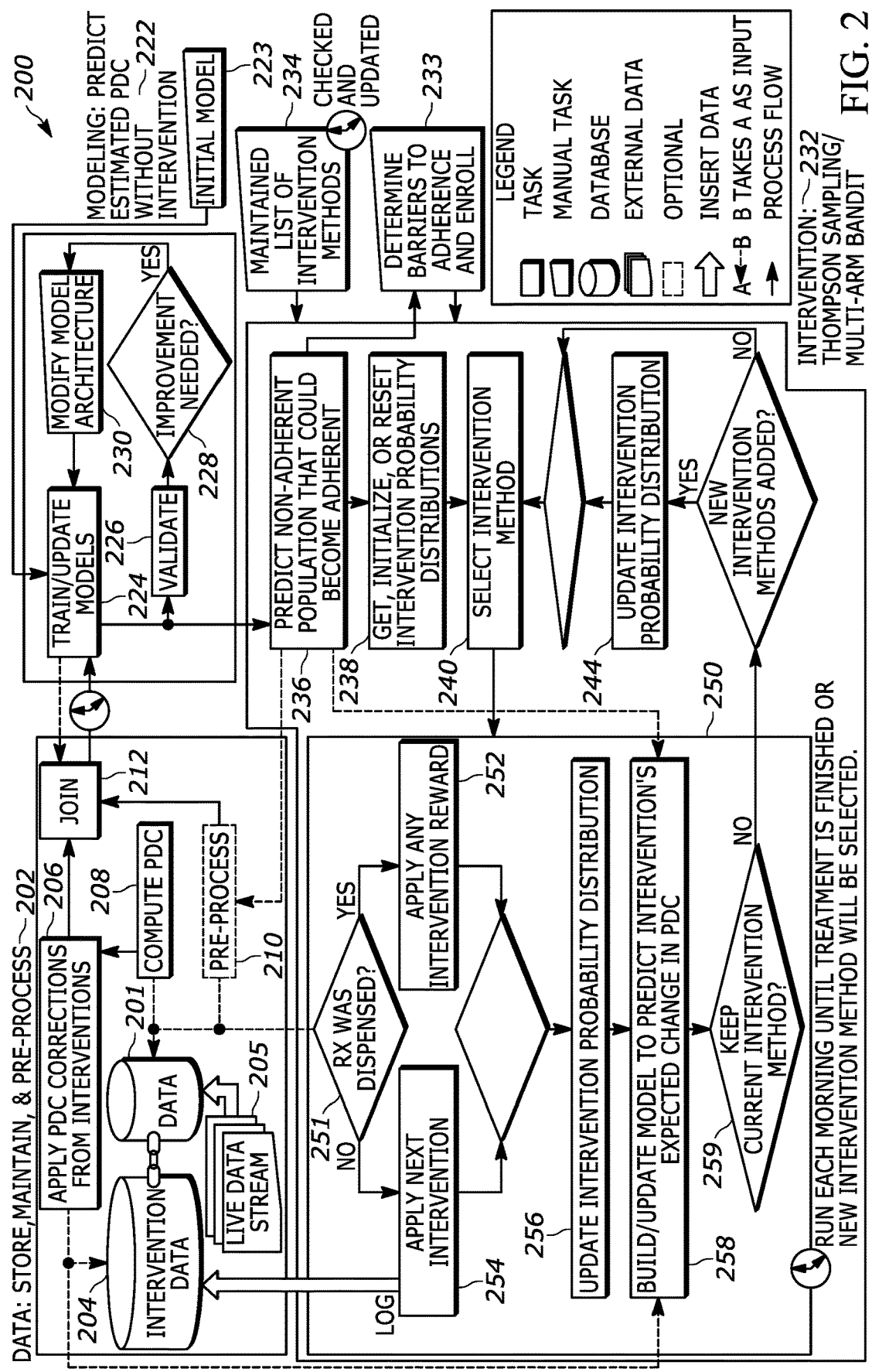
FIG. 2 illustrates a flow diagram depicting an example AI based system implemented as part of the platform of FIG. 1 and configured to implement patient-specific medical adherence intervention, as described in various embodiments herein.

FIG. 2 illustrates a flow diagram depicting an example AI based system 200 implemented as part of the platform 100 of FIG. 1 and configured to implement patient-specific medical adherence intervention, as described in various embodiments herein. For example, AI based system 200 may be implemented on intervention server(s) 102. AI based system 200, executing on server(s) 102, may initiate a correspondence of specific electronic medical adherence intervention communication(s) to medical devices (e.g., mobile devices 111*m* and 113*m*) of various medical patients. As described herein, the correspondence may include information regarding administration of one or more medication for treatment(s) of respective medical condition(s) specific to such patients.

As illustrated in FIG. 2, AI based system 200 comprises three overarching software components or modules that operate or interact together to implement patient-specific medical adherence intervention. These include the data component 202, modeling component 222, and the intervention component 232. Each of these components are software components that include computer instructions and that may be implemented or executed by intervention server(s) 102 of FIG. 1. FIG. 2 also includes a legend that indicates various components of the AI based system 200, including interaction and data access among the various components.

Generally, the data component 202 stores data (e.g., in database 105 and/or memories 106), and periodically prepares such data for training and updating models. Modeling component 222 uses the data to train or update medical adherence AI models and/or modify model architectures to enhance the effectiveness and predictive accuracy of such AI models. In addition, in some embodiments, modeling component 222 is generally responsible for predicting or initiating an estimated PDC (e.g., for example, in embodiments where there has been no previous intervention with specific patient(s)).

Intervention component 232 generally comprises using current iteration(s) of trained medical adherence AI models to interact with and correspond to medical patients, as described herein. Intervention component 232 analyzes existing intervention communications or procedures, performs continual analytics of new/existing intervention communications or procedures, and develops a predictive model(s) (e.g., medical adherence AI model(s)), which may be used for estimating an intervention communication or procedure effect on the PDC of specific patients or cohorts/groups of patients. In various embodiments, intervention component 232 may implement Thompson sampling to determine AI models or actions to solve the exploration-exploitation dilemma in a multi-armed bandit problem for a specific patient or cohort/group of patients. For example, multiple or different intervention communications may be chosen to maximize the expected adherence of a specific patient or cohort/group of patients for given iterations of AI based system 200, across its various components, and/or versions of AI models as described herein.

In various embodiments, after initializing each of the data component 202, the modeling component 222, and the intervention component 232, these components are designed to operate semi-independently, allowing for agile development and improvement/updating of the components, e.g., each at different times and/or with different priorities.

Data component 202 of AI based system 200 stores and collects data for implementing or initiating models (e.g., by modeling component 222). For example, the data may be stored in database 201 or database 204, which correspond to database 105 and/or respective 106 as described herein. Database 201 generally stores live data stream 205 information that includes data, including patient data, medication data, and/or other related data as described for FIGS. 3 and/or 4. Database 204 stores result set data regarding tracking data and information regarding medical adherence by patient(s) based on correspondence of the electronic medical adherence intervention communications as described herein. For example, new medication data may be stored into database 201. Such data may then be linkable or accessible the intervention data (e.g., in database 204), which may be produced by intervention component 232 (or vice versa), so that for each medication filled/dispensed, for a given patient, AI based system 200 can determine if there was an interaction by or intervention for the patient.

Data component 202 of AI based system 200 prepares data (e.g., of database 201 and database 204) for training AI models, e.g., by applying PDC corrections from past interventions/communications (206). Such PDC corrections may be applied to initial PCD computations (208) performed, e.g., by server(s) 102, to determine a baseline PDC value. For example, at block 206, data component 202 may apply/compute corrections to measured PDCs to account for intervention correspondences that have been performed. The PDC correction prepares a PDC value for modeling component 222 and allows modeling component 222 to predict the PDC in the absence of intervention. In some embodiments, the prediction may involve preprocessing, including AI based system 200 reducing the measured PDC of a patient and/or medication for a received intervention correspondence by the intervention method/type's expected change in PDC.

Data component 202 of AI based system 200 may compute the PDC (208) periodically (e.g., daily, weekly, monthly, etc.). If any interventions were performed during a given time period, then the expected change in PDC from the intervention is subtracted from the measured PDCs. Additionally, or alternately, the independent data may be pre-processed (210), e.g., compressed or transformed for use by modeling component 222. Such data may be joined 212 with PDC corrections (206) for using by modeling component 222. For example, after each periodic update of the data (e.g., daily, weekly, monthly, etc.), the modeling component 222 can be initiated by AI based system 200 to update or train AI models as described herein.

In various embodiments, modeling component 222 of AI based system 200 predicts PDC values in the absence of intervention correspondence with given patient(s). Such predicted PDC values could be determined, by modeling component 222, over a calendar year, a single prescription fill, or continuously with time with respect to patient/medication groupings. Generally, modeling component 222 is initiated or executed to create a set of patient/medications, or otherwise identify patient/medications groupings that are expected to be non-adherent. As the term is used herein "patient/medication" may refer to a patient and/or a medication, or a grouping comprising a patient or set of patients with a medication or a set of medications.

AI based system 200 trains AI models (e.g., medical adherence AI models), as described herein, on data and PDC values received or accessed from data component 202. An AI model may be trained or updated (224) on a model architecture (e.g., initial model 223) using the most recently processed data. The output or results of the trained or updated models may then be validated (226) by analyzing error reports, visualizations, and summaries, as generated by AI based system 200. If an improvement is needed (228), e.g., the error rate breaches or exceeds an error threshold, then the model architecture may be modified/updated and a new model may be trained or updated (224) in a further iteration. One or multiple such iterations may be implemented to train or update an AI model (e.g., a medical adherence AI model) as described herein.

Figure 4:
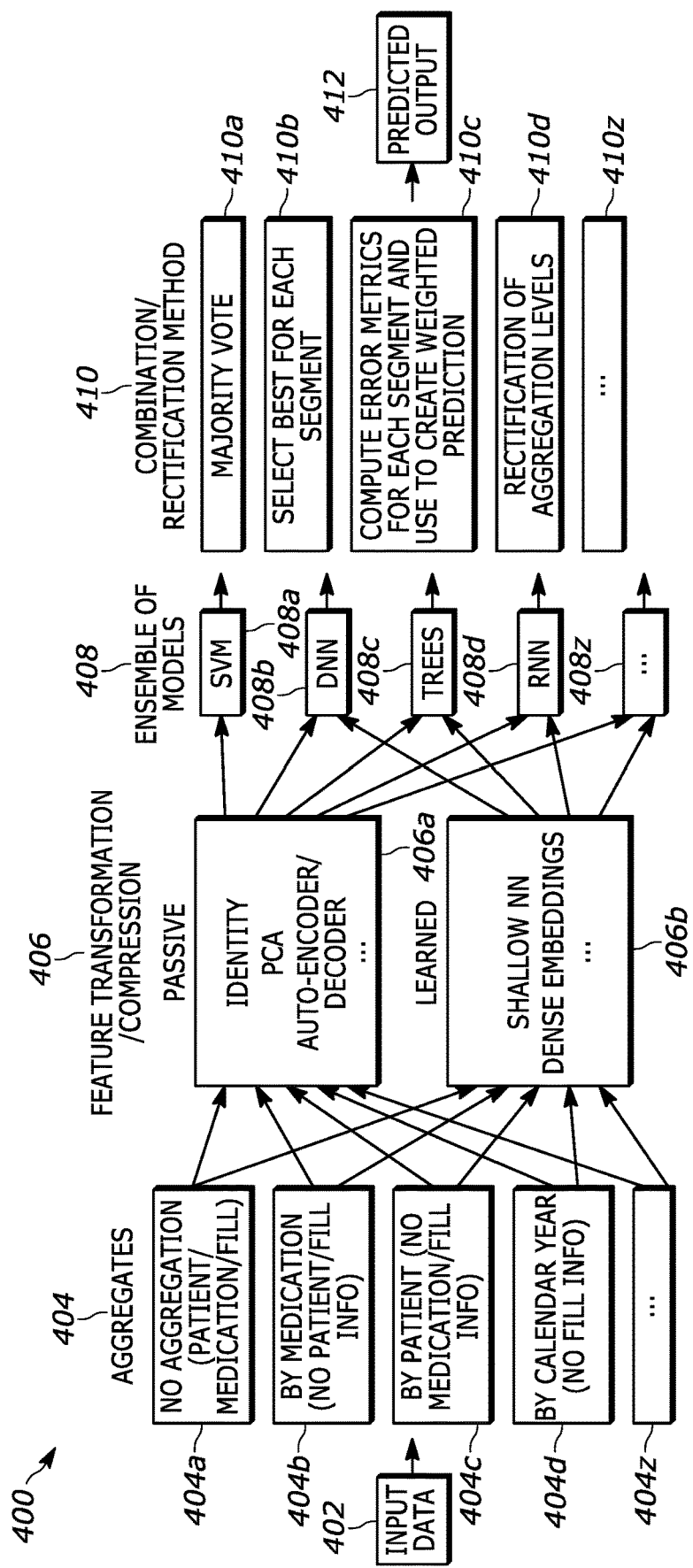
FIG. 4 illustrates a flow diagram depicting an example AI model architecture, in accordance with various embodiments disclosed herein.

In some embodiments, modeling component 222 builds, generates, and/or updates an AI model based on an initial model 223. For example, initial model may be generated or selected from a base AI model architecture. For example, FIG. 4 illustrates a flow diagram depicting an example AI model architecture 400. AI model architecture 400 may be used to generate or update medical adherence AI model(s) as describe herein. AI model architecture 400 may also be modified (230) by modeling component 222 as described herein.

As shown in FIG. 4, AI model architecture 400 includes four primary components or layers, including an aggregation layer 404, a feature transformation/compression layer 406, a model ensemble layer 408, and a combination/rectification layer 410. Each of these layers are software layers that include computer instructions and that may be implemented or executed by processor 104 of intervention server(s) 102.

AI model architecture 400 improves over conventional AI models that rely on a single aggregation or transformation/compression method with a single model. This is because such conventional AI models can be extremely difficult to design and tune to perform across various data samples (e.g. patient/medication combinations). AI model architecture 400 improves over the conventional AI models by implementing an ensemble based framework that uses multiple aggregation techniques (e.g., via aggregation layer 404), multiple transformation/compression techniques (e.g., via aggregation layer 404), an ensemble of different models (e.g., via model ensemble layer 408), and a unification technique (e.g., via combination/rectification layer 410) to combine the large number of resulting predictions into a single predicted output. AI model architecture 400 allows for server(s) 102 to create an overall model that has the ability to accurately predict and generalize to new data for the majority (if not all) data samples. This not only improves the accuracy of server(s) 102, but also reduces the memory and/or processing requiring, over time, as the AI model architecture 400 is able to more quickly, and effectively, determine an accurate predictive model with respect to implementing patient-specific medical adherence intervention.

As illustrated by FIG. 4, AI model architecture 400 is configured to input data (402) into aggregation layer 404. The data may be input by server(s) 102 from database 105 or other databases as described. Server(s) 102 inputs the data into aggregation layer 404 for the purpose of creating different data aggregates separated by data categories. These data aggregates/categories could be, for example, by medication 404b, which would provide data for predicting a single PDC for each medication. Additionally, or alternatively, a data aggregate or category could be determined by server(s) 102 based on patient data 404c, which would provide data for predicting a single PDC for each patient (e.g., regardless of medication). Other data aggregates/categories could also be generated or determined, including, by time period 404d (e.g., calendar year), no-aggregation 404l (e.g., all data used), or other such combinations of data 404z.

Server(s) 102 may then provide the data aggregates/categories of layer 404 to transformation/compression layer 406 of AI model architecture 400. Generally, transformation/compression layer 406 layer can be subdivided into two different groups: passive data 406a and learned data 406b. The passive data group comprise transformations/compressions that are static and do not need to be learned by models implement layer 406. For example, data regarding principle component analysis (PCA) and compression using an autoencoder/decoder would belong to passive data 406a. Additionally, or alternatively, learned data 406b comprises transformation/compression data that is learned, e.g., via AI models. Such data could be, for example, learned or generated via shallow neural network (NN) for feature transformation, or learned or generated via one or more dense embedding layers based on the input data (medication type, patient ID, etc. as described herein for FIG. 3). Any dense embedding layers could be averaged or otherwise automatically determined, e.g., by server(s) 102, by patient/medication features to build estimates for new patient(s), existing patient(s), and/or medications.

Server(s) 102 may then provide the passive data 406a and learned data 406b to model ensemble layer 408 of AI model architecture 400. Each of the aggregated and transformed/compressed data sets, as determined by layers 404 and/or 406, may then be used to train an ensemble of models with different AI algorithms that may each comprise various architectures and/or hyper-parameters. These various AI algorithms could include K-nearest neighbors (KNN), support vector machines (SVM) 408a, deep neural nets (DNN) 408b, various decision trees 408c, random forests, XGboost, or recurrent neural nets (RNN) 408d, or other such AI algorithms 408z.

Server(s) 102 may then provide the results or output of ensemble layer 408 to the combination/rectification layer 410 of AI model architecture 400. For example, the output or results from the ensemble of models trained on each set of aggregated and transformed/compressed data sets may then be combined/rectified, e.g., by server(s) 102, to produce a single predicted output 412. Such output is typically more accurate, and at least more robust, than each of individual models alone. The combination/rectification layer 410 may generate its predicted output 412 via a variety of techniques, including a majority vote of the models or AI algorithms of ensemble layer 408. Additionally, or alternatively, server(s) 102 may determine predicted output 412 by estimating each of the models errors, of ensemble layer 408, on a given data segment and then use these errors to produce a weighted mean. Additionally, or alternatively, server(s) 102 could rectify (e.g., at layer 410) different aggregation levels (e.g., from layer 404) to produce a single prediction (412) at the patient/medication level.

Referring to FIG. 2, intervention component 232 is configured to continually and/or automatically determine effective intervention methods/types, including electronic medical adherence intervention communications, intervention channels, templates, etc. as described herein, for each patient/medication segment/group/cohort and/or specific patient. In addition, in various embodiments, intervention component 232 generates a time dependent or iterative predictive model that estimates an expected change in PDC for each interaction method for each patient/medication segment and/or specific patient. For example, in one embodiment, on a given iteration, a new medication for diabetes may be introduced. For example, data for the new mediation may be added to database 201 and/or database 204 as medication features (312) as described herein. The new medication features (312) may be used to train a medical adherence AI model (e.g., a medical adherence AI model 108) to update the model such that the model's output and/or predictions determine, select, or otherwise accurately identify intervention template(s), intervention channel(s) appropriate for the new medication, and for given patient types or groups, for generation of electronic medical adherence intervention communications for correspondence to new or existing medication patients of patient types or groups, etc., as described herein. For example, when a new medication is introduced into AI based system 200, its new medication features (312) will be added to database 201 and/or database 204). In some embodiments, during a first iteration upon the introduction of the new medication features (312), there may be little or no information or data regarding which intervention templates and/or templates would be likely be effective for medical adherence. Nonetheless, during such first iteration, an AI model (e.g., AI model 108), may be trained with the new medication features (312) and/or at least used to predict the intervention template(s) and/or channel(s) that may be effective for a given patient or patient group associated with a prescription for the new mediation. For example, in embodiments where the AI model 108 is not yet trained with new medication features of a new medication (e.g., during a first iteration), AI model 108 may predict the intervention template(s) and/or channel(s) that would likely be effective, for a given patient or patient group associated with a prescription for the new mediation, based on a similarity of the new medication features with existing medication features (312). In particular, in such embodiments, AI model 108 determines that intervention templates and/or templates that are effective for an existing medication with similar medication features as those of the new medication will likely also be effective for the new medication. In additional embodiments, in a second iteration through AI based system 200 regarding the new medication, AI based system 200 would have both the new medication features (312) of the new medication and also data regarding how patients responded or reacted (or did not respond or react) to specific intervention templates, channels, and/or communications. Such information could then be used to train or update an AI model (e.g., AI model 108) to improve the accuracy of the AI model, and ultimately AI based system 200, to make enhanced predictions as to effective templates, channels, and/or communications, e.g., to improve medical adherence rates for new patients or patient groups that have been prescribed the new medication.

Generally, intervention component 232 is initiated several inputs. For example, a first input includes a set of patient/medication data defining medical patients that should be targeted for medical adherence intervention, as described herein. In a first iteration of AI based system 200, a first set of patient/medication data could define all known patients, or, alternatively, all expected non-adherent patients. Additionally, or alternatively, if an initial data set (as of a given time or iteration) has been influenced by past or current interventions and related communications, then a further input may comprise a updated, expected change in PDC for each new past or current intervention, as computed at blocks 206 and/or 208 as described herein. Additionally, or alternatively, a further input may comprise an initial set of intervention methods/types (block 234), which may include an initial set of intervention templates, channels, communications, etc. as described herein.

In some embodiments, a set of given intervention methods/types (block 234) are determined for a specific patient, e.g., by intervention server(s) 102, based on communication/contact barriers to adherence and enrollment (block 233). For example, intervention server(s) 102 may track or store barriers for specific patients or general barriers as established by legal regulations. For example, barriers may include whether intervention server(s) 102 are allowed to contact a patient regarding intervention. Additionally, or alternatively, a barrier (or, relatedly, a permissive use), as stored or maintained by intervention server(s) 102, may determine or track whether a patient has consented (e.g., via an electronic submission) to receiving intervention via a particular contact channel. In addition, intervention server(s) 102, may store or track communication methods that available for a particular patient (e.g., does the user have a computer, phone, mobile device) and/or other details of the patient (e.g., demographics and the like). Such information may be obtained during an information gathering and enrolling session (block 233), where intervention server(s) 102 may receive the information from a patient via an web browser, mobile app (e.g., medical adherence application), telephone communication, or other such enrollment or data gather interface, application, or the like.

In various embodiments, intervention component 232 takes the above referenced inputs and executes the following algorithm. At block 236, for a given iteration of AI based system 200, intervention server(s) 102, implementing medical adherence artificial intelligence model 108, predicts a non-adherent patient population that may become adherent with medical adherence intervention. That is, the output of medical adherence artificial intelligence model 108 comprises a set or list of patient/medications expected, e.g., as determined by train medical adherence artificial intelligence model 108, to be non-adherent without intervention, but potentially adherent with intervention. The set or list or set or list of patient/medications may be filtered or refined, e.g., by intervention server(s) 102 a set of communication barriers (block 233) that patients face to becoming adherent. Such barriers may be removed or eliminated by enrolling a given patient in additional forms of communication (text/email/in-app communications), and receiving, at intervention server(s) 102, patient permission to intervene. Intervention server(s) 102 may store the permissions and barriers in database 105 and/or memorie(s) 106.

At block 238, for each patient/medication, intervention server(s) 102 determines the probability distribution of the intervention methods/types that maximizes an expected increase in PDC, for a specific patient or group of patients, while also exploring new intervention methods/types for the specific patient or group of patients. In some embodiments, if a distribution has not yet been initialized, or a signal has been sent to reset it, server(s) 102 may re-initialize the distribution. For example, initializing or updating a given intervention's probability distribution for selecting a given intervention method/type for a specific patient or group of patients generally involves server(s) 102 segmenting the patient/medication population data into discrete groups to create groups of patients with a same effective barrier and/or same intervention method/type. In some embodiments, server(s) 102 may further segment the patient/medication population data by patient and across at least two sub-groups: patients who have self-identified as having a specific communication/channel barrier and those who have not so self-identified. Server(s) 102 analyzes the distribution of barriers in the self-identified sub-group to infer the distribution of barriers in the non-self-identified group. Server(s) 102 may then generate a set or list of intervention types/methods specifically created for overcoming each barrier, for each specific patient and/or group of patients, based on the probability of overcoming such barriers. In some embodiments, server(s) 102 initializes each such intervention type/method with equal probability. Initializing, determining, or updating such probability distributions may be performed by intervention server (s) 102, across one or more iterations, after measuring the success or failure of a given type/method for a specific patient or patient group. Server (s) 102 may determine the probability distribution(s) using Bayesian methods, Thomson sampling, epsilon greedy, upper confidence bounds algorithms, etc.

At block 240, intervention server(s) 102 (e.g., via AI model 108) selects an intervention method/type, for example, by sampling from the probability distribution as determined, initialized, updated, etc., as described for block 238.

Intervention methods/types may comprise the generation, by intervention server(s) 102, of electronic medical adherence intervention communication corresponding to specific intervention channels and based on templates as described herein. Intervention server(s) 102 may initiate correspondence of such electronic medical adherence intervention communications to specific patients or patient groups/categories/cohorts.

Once one or more intervention methods/types are selected (block 24), server(s) 102 may execute intervention algorithm 250. Intervention algorithm 250 may be executed at specific or batch time periods (e.g., once a morning) until a treatment for a specific patient is finished or a new intervention method is selected (based on further iterations of AI based system 200) for the specific patient.

For any given iteration or time period, at block 251, intervention server(s) 102 begins execution of intervention algorithm 250 by accessing or reading data (e.g., from database 201 and/or database 204) regarding the patient or patient group and/or medication type(s). Intervention component 232 considers a successful intervention methods/type where the patient exhibited medical adherence. This may be demonstrated by a patient refilling (or having dispensed) a given medication. At block 252, if a medication of patient was dispensed, then intervention server(s) 102 sends or stores a reward (if any) corresponding to the intervention method or type. At block 254, however, if a medication of patient was not dispensed, then apply the next intervention, which might be none for the current time period or batch.

Intervention component 232 may consider various intervention methods/types, including electronic medical adherence intervention communications as transmitted to or otherwise provided to medical patients. For example, such electronic medical adherence intervention communications ma include any of a phone call by pharmacist, a robotic based call, e.g., initiated by intervention server(s) 102, a text message transmitted from intervention server, an in-app communication transmitted from intervention server(s) 102, an email transmitted by intervention server(s) 102, and/or direct mail as initiated by intervention server(s) 102. For each of these contact channels and communication types, the content of the intervention message, e.g., via interaction templates, may be fine-tuned, by intervention server(s) 102, to specific patients or patient groups/cohorts, e.g., the correspondence or communications stylized or formatted to be alarmist vs. gentle persuasion; succinct vs. verbose; black & white vs. color images, choice of creative, etc.

Generally, the available forms of correspondence and/or communication (i.e., those not prohibited by barriers) impacts the opportunity for moving a patient from a non-adherent state to an adherent state. For example, a patient that has allowed or selected many preferred channels or communication types will allow intervention component 232 to have a higher likelihood of selecting an intervention type/method that will cause the patient to medically adhere.

In some embodiments, a medical adherence communication may be implemented or initiated only if it is feasible for a given intervention channel. For example, if a patient can only be called, then, due to the general cost of a call (e.g., having a pharmacist call), then only those patients with a high confidence of adherence after receiving a call may be targeted by intervention component 232. If a patient accepts text messages or emails, then the number of interactions that can be made by intervention component 232 greatly increases. In such embodiments, because of the reduced cost of text messages, a lower probability of patient adherence may be required for intervention component 232 to initiate the correspondence/communication. As a further example, if a patient has mobile app, then the mobile may receive push notifications regarding medical adherence. In such embodiments, daily interactions with the patient (reminding them to take their pills, for example) may be performed by intervention component 232.

Intervention component 232 may consider demographic data (e.g., from database 201 and/or database 204) in determining which intervention methods/types to communicate to a given medical patient. For example, depending on the demographics of the patient, different intervention channels may be more effective at making the patient medically adhere. For example, an older generation may be more comfortable with phone calls with a pharmacist, working adults may become upset if they get a phone call during the day, but pleased with well-worded, short text message. Once a correct intervention channel is determined, intervention server(s) 102 may correlate the channel to an effective interaction method/type, including determining the content of the message (e.g., as determined by various intervention templates). Intervention server(s) 102 may determine different templates for respective patients over multiple iterations of example AI based system 200 and via a patient profiling of patient data, as stored in database 201 and/or database 204. Such data may include what products the patient buys, what is the age of the patient, gender, and other such behavior and/or demographic data of the patient.

At block 256, intervention server(s) 102 executes algorithm 250 to update the probability distribution based on whether the medication of patient was dispensed as determined for blocks 251, 252, and 254. For example, if intervention server(s) 102 detects a dispensing of the medication for the given intervention method/type, then the probability is increased for that intervention method/type. However, if intervention server(s) 102 fails to detect a dispensing of the medication (e.g., the patient did not adhere) for the given intervention method/type, then the probability is decreased for that intervention method/type.

At block 258, intervention server 102 executes algorithm 250 to train, retrain, or update a medical adherence AI model to provide improved predictions regarding a new expected change in PDC for each intervention method or type for each patient/medication. If a new intervention method/type should be selected mid-treatment, i.e., during execution of executes algorithm 250, (e.g., by determination at block 240, during a new iteration of AI based system 200, of an improved or more accurate intervention method/type), then intervention server(s) 102 may restart algorithm 250 to begin using the improved intervention method/type. Otherwise algorithm 250 may continue to a next time period, using the current intervention method/type, for example, until the treatment is finished.

Generally, server(s) 102, and medical adherence artificial intelligence model 108, enhance patient medical adherence by determining the intervention method/type corresponding to a patient's cause of non-adherence. On the other hand, an intervention method/type at odds with the patient may result in a further decrease in PDC for the patient. For any given patient, AI based system 200 may store (e.g., in database 201 and database 204) various conditions causing a patient to be non-adherent. For example, one condition may include whether a patient typically forgets to take a medication. For such patients, a communication including reminder(s) through a mobile app or SMS may yield higher medical adherence.

As another example, another condition may include whether a patient considers it unimportant to take a prescribed medication. For such patients, educational communications may be transmitted to explain why the medication is beneficial to the patient. For example, a pharmacist call or informational email could be transmitted to the patient's mobile device (e.g., mobile device 111m).

As another example, another condition may include whether a patient did not want to travel to pick up a medication from the pharmacy? For such patients, a personalized reason to travel to a store may be communicated and/or an educational message may be transmitted a mobile device (e.g., mobile device 111m) regarding the importance of taking a medication. Delivery options may also be communicated to the patient via a mobile device (e.g., mobile device 111m).

As further example, another condition may include whether a patient can afford a medication. For such patients, educational communications may be transmitted that may identify whether there are cheaper (e.g., generic) alternative medications. Additionally, or alternatively, a personalized discount may be transmitted to the patient's mobile device.

Through the patient's demonstrating (or not demonstrating) adherence after receiving various forms of invention methods/types, through various channels and/or generated with various templates, AI based system 200 implements a dynamic and recurrent analysis of medical intervention. This, coupled with customer profiling and data collection, example AI based system 200 to learn, over multiple iterations of improved medical adherence artificial intelligence models, which communication types more accurately impact which customer segments, allowing for increased adherence.

At block 259, if any new intervention method/types have been added, then intervention server(s) 102, at block 244, updates the probabilities for the selection of each new intervention method. The updated probabilities may then be used to select a new, improved, or updated invention method/type in a future iteration of AI based system 200.

Once algorithm 250 completes, intervention component 232 may initiate a next iteration, including intervention server(s) 102 beginning execution at data component 202, then to modeling component 222, and to intervention component 232, including at block 236 to block 240 and selecting a possible improved or updated intervention method/type.

Figure 5:
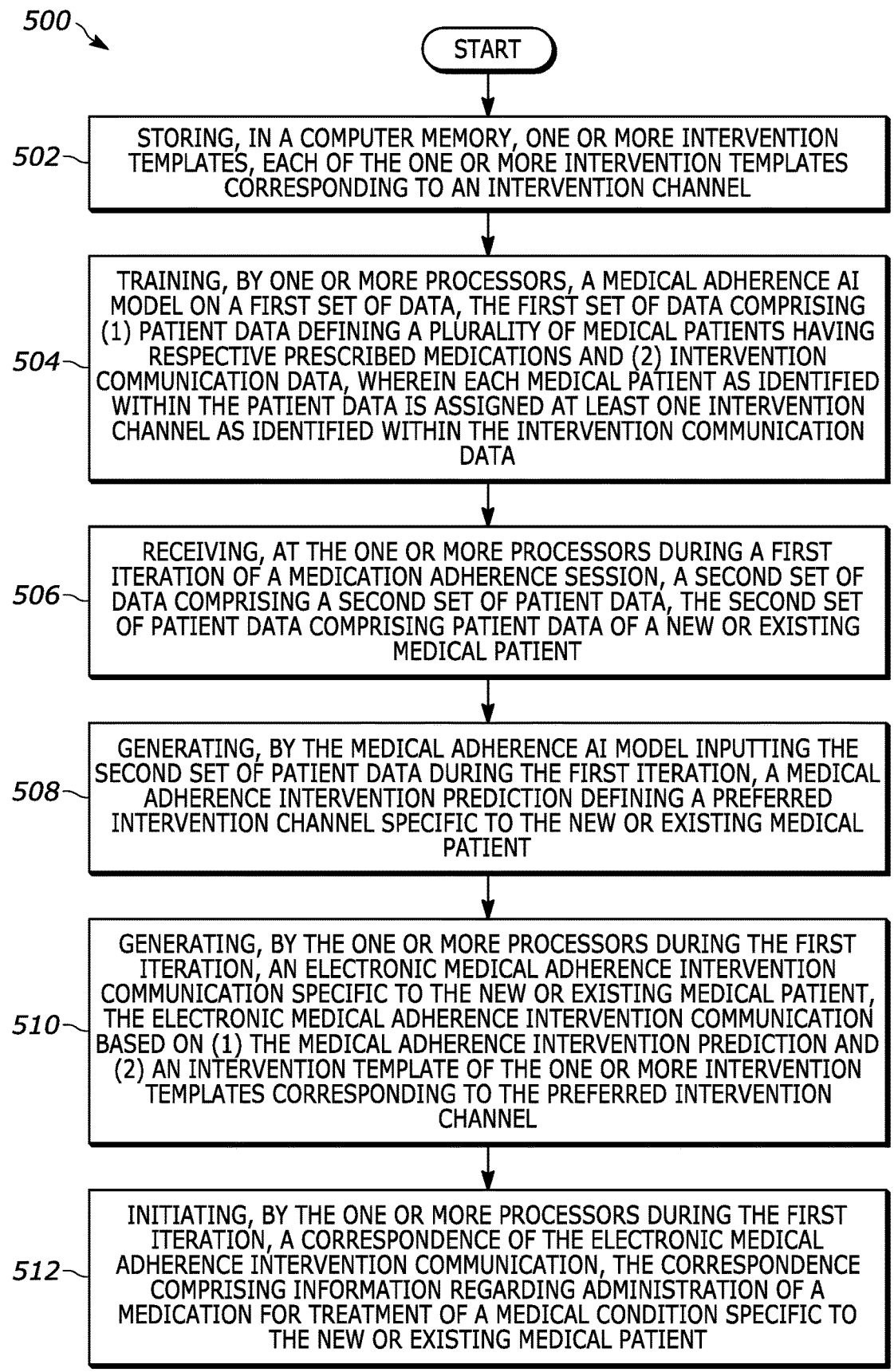
FIG. 5 illustrates an example AI based method for implementing patient-specific medical adherence intervention, in accordance with various embodiments disclosed herein.

FIG. 5 illustrates an example AI based method 500 for implementing patient-specific medical adherence intervention. In various embodiments, AI based method 500 may comprise, for example, an algorithm implemented by intervention server(s) 102. At block 502, AI based method 500—may include storing, in a computer memory (e.g., aggregation layer 404), one or more intervention templates. In some embodiments, the one or more intervention templates may include electronic message content particular to a specific patient cohort and the medication. In addition, each of the one or more intervention templates may correspond to an intervention channel. An intervention channel may comprise at least one of: a telephone communication, a text message, an in-app communication, or an email. Generally, for each channel, server(s) 102 may combine data with templates to fine-tune and personalize the content of an intervention message for specific patient types and/or known patient behavior types and/or preferences (e.g. alarmist vs. gentle persuasion; succinct vs. verbose; black & white vs. color images, choice of creative, etc.).

At block 504, AI based method 500 may further include training, by one or more processors, a medical adherence AI model on a first set of data. The first set of data may comprise any of the data as described for FIG. 4 or as otherwise described herein. The first set of data may comprise (1) patient data defining a plurality of medical patients having respective prescribed medications and (2) intervention communication data. Each medical patient, as identified within the patient data, may be assigned to at least one intervention channel, as identified within the intervention communication data. In some embodiments, at least a portion of the first set of data may comprise compressed and/or transformed feature data, for example, as described herein for FIG. 4.

At block 506, AI based method 500 may further include receiving, at the one or more processors during a first iteration of a medication adherence session, a second set of data comprising a second set of patient data. The second set of patient data may comprise patient data of a new or existing medical patient. For example, a new medical patient is a patient who has at least some data or information (e.g., patient data, medication data, identified or preferred intervention template(s), identified or preferred intervention channels, etc. as described herein) not yet assigned or entered into AI based system 200, e.g., into database 201 or database 204 as described herein. Whereas an existing medical patient is a patient who has at least some data or information (e.g., patient data, medication data, identified or preferred intervention template(s), identified or preferred intervention channels, etc. as described herein) assigned or entered into AI based system 200, e.g., into database 201 or database 204 as described herein. Additionally, or alternatively, an existing patient may be a patient previously identified, communicated with, or otherwise analyzed by AI based system 200 during a first iteration of a medication adherence session as described herein. Whereas a new patient may be a patient not yet previously identified, communicated with, or otherwise analyzed by AI based system 200 during a first iteration of a medication adherence session as described herein In some embodiments, method 500 may further comprise, intervention server(s) 102, generating the second set of patient data comprising the patient data of the new or existing medical patient. The medical adherence AI model, executing on intervention server(s) 102, may generate a non-adherence prediction indicating that the new or existing medical patient is likely to be non-adherent as to the medication for treatment of the medical condition. In various embodiments, the non-adherence prediction may comprise a PDC prediction or value indicating that the new or existing medical patient is likely to be non-adherent as to the medication for treatment of the medical condition.

In some embodiments, the medical adherence AI model, e.g., as trained at block 504, may comprise an ensemble based model, e.g., as described herein for FIG. 4. In such embodiments, the ensemble based model may be comprised of a plurality of AI algorithms that each input a least a portion of the first set of data (e.g., input data 402). Additionally, or alternatively, each of the AI algorithms may output a predicted value. In such embodiments, the medical adherence intervention prediction may comprise an aggregate prediction based on each predicted value of the AI algorithms (e.g., single prediction 412). For example, as described for FIG. 4, the results from the ensemble of models trained on each set of aggregated and transformed/ compressed data sets may combined/rectified to produce a single predicted output (e.g., single prediction 412), which is more accurate than each of the individual models alone.

At block 508, AI based method 500 may further include generating, by the medical adherence AI model inputting the second set of patient data (e.g., any of the data of FIG. 4) during the first iteration, a medical adherence intervention prediction defining at least a preferred intervention channel specific to the new or existing medical patient. In some embodiments, the preferred intervention channel specific to the new or existing medical patient may include consideration of, or may otherwise comprise, a permissive intervention channel. A permissive intervention channel generally corresponds to communication barriers (232) that patients face to becoming adherent. Overcoming such barriers may require enrolling patients in various forms of communication (e.g., text/email/in-app communications), and getting permission, from a patient or his or her prover to intervene.

At block 510, AI based method 500 may further include generating, by the one or more processors (e.g., of intervention server(s) 102) during the first iteration, an electronic medical adherence intervention communication specific to the new or existing medical patient. In such embodiment, the electronic medical adherence intervention communication may be based on (1) the medical adherence intervention prediction and (2) an intervention template of the one or more intervention templates corresponding to the preferred intervention channel. In some embodiments, intervention server(s) 102 may generate, by the medical adherence AI model, the intervention template based on the first set of data such that the intervention template is a new intervention template specific to the new or existing medical patient. In this way, the AI based system 200 modifies the intervention data population size by receiving each intervention result and, in some embodiments, may use that result to analyze new or emerging intervention templates and related communications.

At block 512, AI based method 500 may further include initiating, by the one or more processors (e.g., of intervention server(s) 102) during the first iteration, a correspondence of the electronic medical adherence intervention communication. The correspondence may comprise information regarding administration of a medication for treatment of a medical condition specific to the new or existing medical patient. In some embodiments, intervention server(s) 102 may transmit the correspondence to an electronic device (e.g., mobile device 111m) of the new or existing medical patient or an electronic a device (e.g., mobile device 113m) of a person associated with the administration of the medication. Additionally or alternatively, the intervention communication is provided to a medical adherence app implemented on a device (e.g., mobile device 111m) of the new or existing medical patient. In various embodiments, the medical adherence app may be a mobile app natively configured and developed for a mobile platform, such as APPLE iOS and/or GOOGLE Android.

In still further embodiments, intervention server(s) 102 may receive medical adherence tracking data from a device (e.g., mobile device 111m) of the new or existing medical patient or from a device (e.g., mobile device 113m) of a person associated with the administration of the medication. In such embodiments, the medical adherence tracking data defines a degree of medical adherence of the new or existing medical patient. For example, the degree of medical adherence may include, or at least be based on PDC, e.g., regarding the fraction of days a patient is covered (has effective medication) to treat a medical condition.

In some embodiments, intervention server(s) 102 generates a reward for the new or existing medical patient when the degree of medical adherence of the medical patient exceeds a predefined medical adherence threshold. Such reward may be stored on a computer memory (e.g., computer memory 106) in an electronic profile associated with the new or existing medical patient.

In some embodiments, method 500 may comprise multiple iterations or round trips through the components (e.g., data component 202, modeling component 222, and intervention component 232) of AI based system 200. For example, in such embodiments, AI based system 200 is configured to automatically and/or continually create and test new intervention correspondences/communications, including when, how, how many times, and in what combinations of interaction modes and intervals to intervene, over time through the multiple iterations. In such embodiments, for method 500, a given electronic medical adherence intervention communication may be a first communication in a series of communications during the medication adherence session. In these embodiments, medical adherence AI model is retrained or updated (e.g., at block 224 of FIG. 2 within modeling component 222) on a third set of data. The third set of patient data may comprise (1) patient data of a plurality of medical patients and (2) intervention communication data. The third set of data may be a new set of data gathered during (or after) the first iteration by data component 202 as described herein. In addition, the third set of data may comprise adherence tracking data of the new or existing medical patient.

Method 500 may include intervention server(s) 102 generating, during a second iteration of a medication adherence session by the medical adherence AI model inputting the third set of patient data, a second medical adherence intervention prediction defining a second preferred intervention channel specific to the new or existing medical patient. In various embodiments, the second preferred intervention channel may differ from the preferred intervention channel of the first iteration.

Method 500 may include intervention server(s) 102 generating, during the second iteration of the medication adherence session, a second electronic medical adherence intervention communication specific to the new or existing medical patient based on the second medical adherence intervention prediction and a second intervention template of the one or more intervention templates corresponding to the second preferred intervention channel. In various embodiments, the second intervention template may differ from the intervention template of the first iteration.

Still further, method 500 may include intervention server(s) 102 initiating, during the second iteration of the medication adherence session, a second correspondence of the second electronic medical adherence intervention communication. The second correspondence may include information regarding administration of the medication for treatment of the medical condition specific to the new or existing medical patient.

CONCEPTS OF THE DISCLOSURE

The below concepts relate to the disclosure herein, and are implemented and/or maintained, either in whole or in part, by AI based system 200, including by its various components.

Independent Features

Various independent features/feature data may be used to predict PDC. Such feature data may broadly include anything of relevance, particularly features concerning the patient, condition, insurance coverage, patient behaviors, and time/geo based features, etc. Example feature data is provided herein as illustrated in FIG. 3.

Project Pillars and Implementation

As used herein, the use of the term "pillars" generally refers or corresponds to the components of AI based system 200 (e.g., data component 202, modeling component 222, intervention component 232). In various embodiments, the disclosure herein generally directs to these components that comprise modeling, intervention, and data. After initializing each component, the components are designed to be semi-independent from one another, allowing for agile development of each at different speeds and with different priorities. The modeling component is generally responsible for predicting an estimated PDC assuming there has been no intervention. The intervention component is generally responsible for the exploitation of proven intervention methods, the continual exploration of new/existing intervention methods, and the development of a predictive model(s) for estimating interventions' effect on PDC value(s). The data component is generally responsible for storing and maintaining the data, and periodically preparing the data for training and updating models. The primary components of each pillar and the interactions between the three components/pillars can be seen in FIG. 2, as described herein.

Modeling Pillar/Component

The modeling component is responsible for predicting the PDC in the absence of interventions. The predicted PDC could be over a calendar year, a single prescription fill, or continuously with time. Generally, the modelling component creates a list of patient/medications that are expected to be non-adherent.

The modeling component is initiated with two required inputs: 1) a very simple initial model architecture must be selected (as described in the Model Architecture section below), and 2) data from the data component as used to train an AI model. After these inputs have been created or otherwise initialized, the flow is as follows:
1. Train the current model architecture using the most recently processed data.
2. Validate the results by building error reports, visualizations, summaries, etc. If improvement is needed, then modify the model architecture and return to step 1.

Modeling Architecture

The proposed modeling architecture comprises four primary components or layers, as graphically depicted in FIG. 4. The general approach of the modeling architecture improves upon use of a conventional, single aggregation or transformation/compression. A single model can be extremely difficult to design and tune so that such single model works for each data sample (e.g. patient/medication combinations). To account for this, the modeling architecture implements or comprises an ensemble framework, using multiple aggregation methods, multiple transformation/compression methods, an ensemble of different models, and then a unification process to combine the large number of resulting predictions into a single predicted output. This approach allows for the creation of an overall model that has the ability to accurately predict and generalize to new data for the majority (if not all) data samples. Given below is the architecture's progression, along with a few examples for each section. These sections are generally illustrated by FIG. 4.

Aggregation

Input data is first sent to an aggregation layer with the purpose of creating different aggregates. These aggregates could be, for example, by medication, which would imply a desired prediction of a single PDC for each medication; or, it could be by patient, which would imply a desired prediction of a single PDC for each patient (regardless of medication).

Transformation/Compression

Each of the computed aggregates is sent to a "Feature transformation/compression" layer. This layer can be sub-divided into two different groups: passive and learned. The passive group comprises transformations/compressions that are static and do not need to be learned with the models that follow this layer; for example, principle component analysis and compression using an auto-encoder/decoder would be in this group. The learned group is generally transformations/compressions which must be learned at the same time as the models that follow; these could be, for example, a shallow neural network (NN) for feature transformation, or one or more dense embedding layers based on the input data (medication type, patient id, etc.). Any dense embedding layers could be averaged by patient/medication features to build estimates for new patients or medications.

Model Ensemble

Each of the aggregated and transformed/compressed data sets is used to train an ensemble of models with different architectures and/or hyper-parameters. These different architectures could be K-nearest neighbors (KNN), support vector machines (SVM), deep neural nets (DNN), various decision trees, random forests, XGboost, or recurrent neural nets (RNN), to name just a few.

Combination/Rectification

The results from the ensemble of models trained on each set of aggregated and transformed/compressed data sets is then combined/rectified to produce a single predicted output, which is better than each of the individual models. These combination/rectification methods could be, for example, a majority vote, or it could estimate each of the models errors on a given data segment and then use these errors to produce a weighted mean, or it could rectify the different aggregation levels to produce a single prediction at the patient/medication level.

Intervention Pillar/Component

The intervention component continually searches for the best intervention method/type for each patient/medication segment while primarily using the best known current intervention methods/types. In addition, this component generates a time dependent predictive model that estimates the expected change in PDC for each interaction method/type for each patient/medication segment.

Generally, the intervention component needs three inputs to initiate: These inputs include (1) A list of patient/medications with whom AI based system 200 should intervene (this could/should even be everybody to start); (2) if any of the initial data (as of today) has been influenced by interventions, then the expected change in PDC for each intervention must be computed (or guessed) by AI based system 200; and (3) An initial set of intervention methods/types, which are described herein, for example, including below herein with respect to Intervention Methods/Types.

With these inputs, the main flow is as follows:
1. Process the results to create the list of patient/medications expected to be non-adherent without intervention, but potentially adherent with intervention.
   a. Output this list to the external module responsible for determining the barriers that patients face to becoming adherent, enrolling them in additional forms of communication (text/email/app based communication), and getting permission to intervene. The results of this module should be fed back into the intervention component, as described herein, for example by Intervention Methods.

2. For each patient/medication get or determine the probability distribution of the intervention methods that maximizes the expected increase in PDC while also exploring new intervention methods. If the distribution has not been initialized, or a signal has been sent to reset it, then (re-)initialize the distribution. This is described further, for example, in Setting/Updating the Intervention's Probability Distribution.
3. Select an intervention method by sampling from the distribution.
4. Start the intervention process: each day (or other time period) do the following until treatment is finished.
A. Read in the most recent data.
B. If a patient's medication/Rx was dispensed, then send out any reward (if any) connected with the intervention method. If the medication/Rx was not dispensed, then apply the next intervention, which might be none for the current day.
C. Update the intervention's probability distribution (if another day late on dispensing, then decrease probability).
D. Train/update a model predicting the expected change in PDC for each intervention method for each patient/medication.
E. If a new intervention method should be selected mid-treatment, then exit loop, otherwise continue to next day until the treatment is finished.
5. If any new intervention methods have been added, then update the probabilities of selecting each intervention method.
6. Return to step 3.

Intervention Methods/Types

AI based system 200 includes an information gathering and enrolling initiative included as part of the intervention component. Communication methods/types typically comprise phone call by pharmacist, robot-call, text message, in-app communications, emails, and direct mails. For each of these contact channels, there is opportunity to fine-tune and personalize the content of the intervention message (e.g. being alarmist vs. gentle persuasion; succinct vs. verbose; black & white vs. color images, choice of creative, etc.).

The forms of communication available will greatly decrease (if few) or increase (if many) the opportunity for moving a patient from non-adherent to adherent. Additionally, the form of communication will determine the monetary cost of the intervention, thereby allowing AI based system 200 to determine whether communication is feasible.

If a patient can only be called, then, due to the cost of a call, AI based system 200 must determine with high confidence that calling this patient will result in the patient becoming adherent. If a patient accepts text messages or emails, then the number of interactions that can be made greatly increases; further, because of the reduced cost of text messages, AI based system 200 does not have to be as sure that the intervention will result in adherence to attempt it. Finally, if the patient has a medical adherence mobile app with push notifications, then AI based system 200 can have daily interactions with them (reminding them to take their pills, for example).

Patient Identification/Demographics

Depending on who the patient is, different intervention methods—and the content of the message—may work more effectively. For example, an older generation may be more comfortable with phone calls with a pharmacist, working adults may become upset if they get a phone call during the day, but pleased with well-worded, short text message.

Even if this question is answered, correlating the answer to an effective interaction method still must be performed. This is accomplished through the intervention component's continual testing methodology coupled with a patient profiling method (what do they buy, what are their age, gender . . . ).

Barriers to Adherence

Other than maximizing the number of communication methods/types, barriers are also important. AI based system 200 may experience the largest increase in adherence when the intervention method/type matches the cause of non-adherence; on the other hand, an intervention method/type at odds with the cause could result in a further decrease in PDC.

Dynamic testing of intervention methods/types as described herein, coupled with customer profiling, will enable AI based system 200 to indirectly learn why different customer segments are non-adherent.

Setting/Updating the Intervention's Probability Distribution

The initializing of a probability distribution for selecting a given intervention method/type is generally twofold. First, a patient/medication population is segmented down into small groups to create groups with the same barrier (and possibly the same intervention method). Within each of these groups, patient data is further broken down into two sub-groups: those who have self-identified as having a specific barrier and those who have not self-identified. The distribution of barriers in the self-identified sub-group is used to infer the distribution of barriers in the non-self-identified group. Second, a list of intervention methods/types is specifically created for overcoming each barrier is initialized with equal probability.

In various embodiments, AI based system 200 generally updates the probability distribution after measuring the success or failure of a method by using Bayesian methods, Thomson sampling, epsilon greedy, upper confidence bounds algorithms, etc.

Data Pillar/Component

The data component stores the data needed for implementing models, prepare the data for training models, and to apply corrections to measured PDCs to account for interventions that have been performed. This PDC correction is related to the modeling component's implementation of predicting the PDC in the absence of intervention, and can be addressed by reducing the measured PDC of a patient/medication that received intervention by the intervention's expected change in PDC.

Besides storing and maintaining data, the data component requires an estimate for the expected change in PDC caused by interventions. The flow of the data component is as follows:

1. New medical data (e.g., Rx/pharmaceutical data) is stored into databases. This data is linkable to the intervention data produced by the intervention component (or vice versa), so that for each prescription/Rx fill/dispense, an intervention server can determine if there was an interaction.
2. Periodically (every day/week/month/etc.), the PDC is computed, e.g., by an intervention server, from the data and if any interventions were performed, then the expected change in PDC from the intervention is subtracted from the measured PDCs. Additionally, the independent data may be pre-processed to prepare for use by modeling component to train AI models as described herein.

3. After each periodic data preparation, a modeling update should be initiated in the modeling component.

ADDITIONAL CONSIDERATIONS

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. An artificial intelligence (AI) based system configured to implement patient-specific medical adherence intervention, the AI based system comprising:
    a computer memory configured to store one or more intervention templates, each of the one or more intervention templates corresponding to an intervention channel;
    an intervention server, comprising one or more processors communicatively coupled to the computer memory, and configured to access the one or more intervention templates;
    a medical adherence AI model trained on a first set of data comprising (1) patient data defining a plurality of medical patients having respective prescribed medications, (2) intervention communication data, (3) data indicating patient responses or reactions to specific intervention templates, (4) data indicating a lack of patient responses or reactions to specific intervention templates, and (5) for each intervention template, the intervention template and the intervention channel specific to the intervention template, wherein each medical patient as identified within the patient data is assigned at least one intervention channel as identified within the intervention communication data; and
    electronic instructions stored on the computer memory that when executed by the one or more processors cause the one or more processors, during a first iteration of a medication adherence session, to:
       receive a second set of data comprising a second set of patient data, the second set of patient data comprising patient data of a new or existing medical patient,
       generate, by the medical adherence AI model inputting the second set of patient data, a medical adherence intervention prediction predicting at least (a) a specific intervention template and (b) a preferred intervention channel specific to the new or existing medical patient, as likely effective for medical adherence by the new or existing medical patient,
       generate an electronic medical adherence intervention communication specific to the new or existing medical patient, wherein generation of the electronic medical adherence intervention communication comprises selecting the specific intervention template as predicted by the medical adherence AI model,
       merge patient specific data of the new or existing medical patient into one or more placeholders or data fields of the intervention template, and
       initiate a correspondence of the electronic medical adherence intervention communication via the preferred intervention channel as predicted by the medical adherence AI model, the correspondence comprising information regarding administration of a medication for treatment of a medical condition specific to the new or existing medical patient,
    wherein the medical adherence AI model comprises an AI model architecture having a plurality of software architecture layers including: (i) an aggregation layer; (ii) a feature transformation/compression layer; (iii) a model ensemble layer; and (iv) a combination/rectification layer, and
    a modeling component comprising computing instructions that when executed by the one or more processors cause the one or more processors to update the medical adherence AI model to output an improved prediction by modifying at least one of the plurality of software architecture layers of the AI model architecture based on (i) the medical adherence intervention prediction of the new or existing medical patient, and (ii) periodic data of other medical patients received during or after the first iteration, wherein the improved prediction comprises a new expected change in proportion of days covered (PDC) for the new or existing medical patient,
    wherein the electronic instructions stored on the computer memory, when further executed by the one or more processors, cause the one or more processors, during a second iteration of a medication adherence session, to:
       based on the improved prediction, initiate a second correspondence of a second electronic medical adherence intervention communication, wherein the second electronic medical adherence intervention communication is sent via a preferred intervention channel and is created with a preferred intervention template, each based on the improved prediction, the second correspondence comprising updated information regarding administration of a medication for treatment of the medical condition specific to the new or existing medical patient.

2. The AI based system of claim 1, wherein the electronic instructions, when executed by the one or more processors during the first iteration of a medication adherence session, further cause the one or more processors to:
    generate the second set of patient data comprising the patient data of the new or existing medical patient, wherein the medical adherence AI model generates a non-adherence prediction indicating that the new or existing medical patient is likely to be non-adherent as to the medication for treatment of the medical condition.

3. The AI based system of claim 1, wherein the medical adherence AI model is an ensemble based model comprised of a plurality of AI algorithms that each input a least a portion of the first set of data, each of the AI algorithms outputting a predicted value, and wherein the medical adherence intervention prediction comprises an aggregate prediction based on each predicted value of the AI algorithms.

4. The AI based system of claim 1, wherein at least a portion of the first set of data comprises transformed feature data.

5. The AI based system of claim 1, wherein the preferred intervention channel specific to the new or existing medical patient comprises a permissive intervention channel.

6. The AI based system of claim 1,
    wherein the electronic medical adherence intervention communication is a first communication in a series of communications during the medication adherence session, wherein the medical adherence AI model is retrained on a third set of data comprising (1) patient data of a plurality of medical patients and (2) intervention communication data, the third set of data comprising adherence tracking data of the new or existing medical patient, wherein the electronic instructions, when executed by the one or more processors during a second iteration of the medication adherence session, cause the one or more processors to:

generate, by the medical adherence AI model inputting the third set of patient data, a second medical adherence intervention prediction defining a second preferred intervention channel specific to the new or existing medical patient, generate a second electronic medical adherence intervention communication specific to the new or existing medical patient based on the second medical adherence intervention prediction and a second intervention template of the one or more intervention templates corresponding to the second preferred intervention channel, and, initiate a second correspondence of the second electronic medical adherence intervention communication, the second correspondence comprising information regarding administration of the medication for treatment of the medical condition specific to the new or existing medical patient.

7. The AI based system of claim 6, wherein the second preferred intervention channel differs from the preferred intervention channel.

8. The AI based system of claim 6, wherein the second intervention template differs from the intervention template.

9. The AI based system of claim 1, wherein the electronic instructions, when executed by the one or more processors, further cause the one or more processors to:

receive medical adherence tracking data from a device of the new or existing medical patient or from a device of a person associated with the administration of the medication, the medical adherence tracking data defining a degree of medical adherence of the new or existing medical patient.

10. The AI based system of claim 9, wherein the electronic instructions, when executed by the one or more processors, further cause the one or more processors to:

generate a reward for the new or existing medical patient when the degree of medical adherence exceeds a predefined medical adherence threshold, the reward stored on the computer memory in a profile of the new or existing medical patient.

11. The AI based system of claim 1, wherein the intervention channel comprises at least one of: a telephone communication, a text message, an in-app communication, or an email.

12. The AI based system of claim 1, wherein the electronic medical adherence intervention communication is provided to a medical adherence application (app) implemented on a device of the new or existing medical patient.

13. The AI based system of claim 1, wherein the electronic instructions, when executed by the one or more processors during the first iteration of a medication adherence session, further cause the one or more processors to:

transmit the correspondence to an electronic device of the new or existing medical patient or an electronic device of a person associated with the administration of the medication.

14. The AI based system of claim 1, wherein the one or more intervention templates comprises message content particular to a specific patient cohort and the medication.

15. An artificial intelligence (AI) based method for implementing patient-specific medical adherence intervention, the AI based method comprising:

storing, in a computer memory, one or more intervention templates, each of the one or more intervention templates corresponding to an intervention channel;

training, by one or more processors, a medical adherence AI model on a first set of data, the first set of data comprising (1) patient data defining a plurality of medical patients having respective prescribed medications (2) intervention communication data, (3) data indicating patient responses or reactions to specific intervention templates, (4) data indicating a lack of patient responses or reactions to specific intervention templates, and (5) for each intervention template, intervention template and the intervention channel specific to the intervention template, wherein each medical patient as identified within the patient data is assigned at least one intervention channel as identified within the intervention communication data;

receiving, at the one or more processors during a first iteration of a medication adherence session, a second set of data comprising a second set of patient data, the second set of patient data comprising patient data of a new or existing medical patient;

generating, by the medical adherence AI model inputting the second set of patient data during the first iteration, a medical adherence intervention prediction predicting at least (a) a specific intervention template and (b) a preferred intervention channel specific to the new or existing medical patient, as likely effective for medical adherence by the new or existing medical patient;

generating, by the one or more processors during the first iteration, an electronic medical adherence intervention communication specific to the new or existing medical patient, wherein generation of the electronic medical adherence intervention communication comprises selecting the specific intervention template as predicted by the medical adherence AI model;

merging patient specific data of the new or existing medical patient into one or more placeholders or data fields of the intervention template; and initiating, by the one or more processors during the first iteration, a correspondence of the electronic medical adherence intervention communication via the preferred intervention channel as predicted by the medical adherence AI model, the correspondence comprising information regarding administration of a medication for treatment of a medical condition specific to the new or existing medical patient, wherein the medical adherence AI model comprises an AI model architecture having a plurality of software architecture layers including: (i) an aggregation layer; (ii) a feature transformation/compression layer; (iii) a model ensemble layer; and (iv) a combination/rectification layer;

updating, by a modeling component, the medical adherence AI model to output an improved prediction by modifying at least one of the plurality of software architecture layers of the AI model architecture based on (i) the medical adherence intervention prediction of the new or existing medical patient, and (ii) periodic data of other medical patients received during or after the first iteration, wherein the improved prediction comprises a new expected change in proportion of days covered (PDC) for the new or existing medical patient; and based on the improved prediction and during a second iteration of a medication adherence session, initiating a second correspondence of a second electronic medical adherence intervention communication, wherein the second electronic medical adherence intervention communication is sent via a preferred intervention channel and is created with a preferred intervention template, each based on the improved prediction, the second correspondence comprising updated information regarding administration of a medication for treatment of the medical condition specific to the new or existing medical patient.

16. The AI based method of claim 15 further comprising generating the second set of patient data comprising the patient data of the new or existing medical patient, wherein the medical adherence AI model generates a non-adherence prediction indicating that the new or existing medical patient is likely to be non-adherent as to the medication for treatment of the medical condition.

17. The AI based method of claim 15, wherein the medical adherence AI model is an ensemble based model comprised of a plurality of AI algorithms that each input at least a portion of the first set of data, each of the AI algorithms outputting a predicted value, and wherein the medical adherence intervention prediction comprises an aggregate prediction based on each predicted value of the AI algorithms.

18. The AI based method of claim 15, wherein at least a portion of the first set of data comprises transformed feature data.

19. The AI based method of claim 15, wherein the preferred intervention channel specific to the new or existing medical patient comprises a permissive intervention channel.

20. The AI based method of claim 15 further comprising generating, by the medical adherence AI model, the intervention template based on the first set of data, wherein the intervention template is a new intervention template specific to the new or existing medical patient.

21. The AI based method of claim 15 further comprising, wherein the electronic medical adherence intervention communication is a first communication in a series of communications during the medication adherence session, wherein the medical adherence AI model is retrained on a third set of data comprising (1) patient data of a plurality of medical patients and (2) intervention communication data, the third set of data comprising adherence tracking data of the new or existing medical patient, generating, during a second iteration of a medication adherence session by the medical adherence AI model inputting the third set of patient data, a second medical adherence intervention prediction defining a second preferred intervention channel specific to the new or existing medical patient, generating, during the second iteration of the medication adherence session, a second electronic medical adherence intervention communication specific to the new or existing medical patient based on the second medical adherence intervention prediction and a second intervention template of the one or more intervention templates corresponding to the second preferred intervention channel, and, initiating, during the second iteration of the medication adherence session, a second correspondence of the second electronic medical adherence intervention communication, the second correspondence comprising information regarding administration of the medication for treatment of the medical condition specific to the new or existing medical patient.

22. The AI based method of claim 21, wherein the second preferred intervention channel differs from the preferred intervention channel.

23. The AI based method of claim 21, wherein the second intervention template differs from the intervention template.

24. The AI based method of claim 15 further comprising receiving medical adherence tracking data from a device of the new or existing medical patient or from a device of a person associated with the administration of the medication, the medical adherence tracking data defining a degree of medical adherence of the new or existing medical patient.

25. The AI based method of claim 15, wherein the intervention channel comprises at least one of: a telephone communication, a text message, an in-app communication, or an email.

26. The AI based method of claim 15, wherein the electronic medical adherence intervention communication is provided to a medical adherence application (app) implemented on a device of the new or existing medical patient.

27. The AI based method of claim 15 further comprising transmitting the correspondence to an electronic device of the new or existing medical patient or an electronic a device of a person associated with the administration of the medication.

28. The AI based method of claim 15, wherein the one or more intervention templates comprises message content particular to a specific patient cohort and the medication.

29. A tangible, non-transitory computer-readable medium storing instructions for implementing patient-specific medical adherence intervention, that when executed by one or more processors cause the one or more processors to:

store, in a computer memory, one or more intervention templates, each of the one or more intervention templates corresponding to an intervention channel;

train, by one or more processors, a medical adherence AI model on a first set of data, the first set of data comprising (1) patient data defining a plurality of medical patients having respective prescribed medications (2) intervention communication data, (3) data indicating patient responses or reactions to specific intervention templates, (4) data indicating a lack of patient responses or reactions to specific intervention templates, and (5) for each intervention template, intervention template and the intervention channel specific to the intervention template, wherein each medical patient as identified within the patient data is assigned at least one intervention channel as identified within the intervention communication data;

receive, at the one or more processors during a first iteration of a medication adherence session, a second set of data comprising a second set of patient data, the second set of patient data comprising patient data of a new or existing medical patient;

generate, by the medical adherence AI model inputting the second set of patient data during the first iteration, a medical adherence intervention prediction predicting at least (a) a specific intervention template and (b) a preferred intervention channel specific to the new or existing medical patient, as likely effective for medical adherence by the new or existing medical patient;

generate, by the one or more processors during the first iteration, an electronic medical adherence intervention communication specific to the new or existing medical patient, wherein generation of the electronic medical adherence intervention communication comprises selecting the specific intervention template as predicted by the medical adherence AI model;

merge patient specific data of the new or existing medical patient into one or more placeholders or data fields of the intervention template; and initiate, by the one or more processors during the first iteration, a correspondence of the electronic medical adherence intervention communication via the preferred intervention channel as predicted by the medical adherence AI model, the correspondence comprising information regarding administration of a medication for treatment of a medical condition specific to the new or existing medical patient, wherein the medical adherence AI model comprises an AI model architecture having a plurality of software architecture layers including: (i) an aggregation layer; (ii) a feature transformation/compression layer; (iii) a model ensemble layer; and (iv) a combination/rectification layer;

update, by a modeling component, the medical adherence AI model to output an improved prediction by modifying at least one of the plurality of software architecture layers of the AI model architecture based on (i) the medical adherence intervention prediction of the new or existing medical patient, and (ii) periodic data of other medical patients received during or after the first iteration, wherein the improved prediction comprises a new expected change in proportion of days covered (PDC) for the new or existing medical patient; and based on the improved prediction and during a second iteration of a medication adherence session, initiate a second correspondence of a second electronic medical adherence intervention communication, wherein the second electronic medical adherence intervention communication is sent via a preferred intervention channel and is created with a preferred intervention template, each based on the improved prediction, the second correspondence comprising updated information regarding administration of a medication for treatment of the medical condition specific to the new or existing medical patient.

30. The non-transitory computer-readable medium of claim 29, wherein the instructions are further executed by one or more processors to cause the one or more processors to generate the second set of patient data comprising the patient data of the new or existing medical patient, wherein the medical adherence AI model generates a non-adherence prediction indicating that the new or existing medical patient is likely to be non-adherent as to the medication for treatment of the medical condition.

31. The non-transitory computer-readable medium of claim 29, wherein the medical adherence AI model is an ensemble based model comprised of a plurality of AI algorithms that each input a least a portion of the first set of data, each of the AI algorithms outputting a predicted value, and wherein the medical adherence intervention prediction comprises an aggregate prediction based on each predicted value of the AI algorithms.

32. The non-transitory computer-readable medium of claim 29, wherein at least a portion of the first set of data comprises transformed feature data.

33. The non-transitory computer-readable medium of claim 29, wherein the preferred intervention channel specific to the new or existing medical patient comprises a permissive intervention channel.

34. The non-transitory computer-readable medium of claim 29, wherein the electronic medical adherence intervention communication is a first communication in a series of communications during the medication adherence session, wherein the medical adherence AI model is retrained on a third set of data comprising (1) patient data of a plurality of medical patients and (2) intervention communication data, the third set of data comprising adherence tracking data of the new or existing medical patient, wherein the instructions are further executed by one or more processors to cause the one or more processors to:

generate, during a second iteration of a medication adherence session by the medical adherence AI model inputting the third set of patient data, a second medical adherence intervention prediction defining a second preferred intervention channel specific to the new or existing medical patient, generate, during the second iteration of the medication adherence session, a second electronic medical adherence intervention communication specific to the new or existing medical patient based on the second medical adherence intervention prediction and a second intervention template of the one or more intervention templates corresponding to the second preferred intervention channel, and, initiate, during the second iteration of the medication adherence session, a second correspondence of the second electronic medical adherence intervention communication, the second correspondence comprising information regarding administration of the medication for treatment of the medical condition specific to the new or existing medical patient.

35. The non-transitory computer-readable medium of claim 34, wherein the second preferred intervention channel differs from the preferred intervention channel.

36. The non-transitory computer-readable medium of claim 34, wherein the second intervention template differs from the intervention template.

37. The non-transitory computer-readable medium of claim 29, wherein the instructions are further executed by one or more processors to cause the one or more processors to receive medical adherence tracking data from a device of the new or existing medical patient or from a device of a person associated with the administration of the medication, the medical adherence tracking data defining a degree of medical adherence of the new or existing medical patient.

38. The non-transitory computer-readable medium of claim 37, wherein the instructions are further executed by one or more processors to cause the one or more processors to generate a reward for the new or existing medical patient when the degree of medical adherence exceeds a predefined medical adherence threshold, the reward stored on the computer memory in a profile of the new or existing medical patient.

39. The non-transitory computer-readable medium of claim 29, wherein the intervention channel comprises at least one of: a telephone communication, a text message, an in-app communication, or an email.

40. The non-transitory computer-readable medium of claim 29, wherein the electronic medical adherence intervention communication is provided to a medical adherence application (app) implemented on a device of the new or existing medical patient.

41. The non-transitory computer-readable medium of claim 29, wherein the instructions are further executed by one or more processors to cause the one or more processors to transmit the correspondence to an electronic device of the new or existing medical patient or an electronic a device of a person associated with the administration of the medication.

42. The non-transitory computer-readable medium of claim 29, wherein the one or more intervention templates comprises message content particular to a specific patient cohort and the medication.

* * * * *